United States Patent
Baghel et al.

[11] Patent Number: 5,996,423
[45] Date of Patent: *Dec. 7, 1999

[54] PASSIVE WATER SAMPLER AND METHOD OF SAMPLING

[75] Inventors: Sunita Singh Baghel, Rensselaer; Angelo Anthony Bracco, Albany; Patricia Denise Mackenzie, Clifton Park, all of N.Y.

[73] Assignee: General Electric Company, Schenectady, N.Y.

[ * ] Notice: This patent is subject to a terminal disclaimer.

[21] Appl. No.: 09/167,022

[22] Filed: Oct. 6, 1998

[51] Int. Cl.⁶ ........................................... G01N 1/22
[52] U.S. Cl. ........................................... 73/863.23
[58] Field of Search .................. 73/863.21, 863.23, 73/864.51

[56] References Cited

U.S. PATENT DOCUMENTS

| | | |
|---|---|---|
| 4,078,433 | 3/1978 | McCabe, Jr. et al. . |
| 5,147,561 | 9/1992 | Burge et al. . |
| 5,235,863 | 8/1993 | Bailey et al. ........................ 73/863.21 |
| 5,454,275 | 10/1995 | Kabis . |
| 5,804,743 | 9/1998 | Vroblesky et al. .................. 73/863.23 |

*Primary Examiner*—Robert Raevis
*Attorney, Agent, or Firm*—Ernest G. Cusick; Noreen C. Johnson

[57] ABSTRACT

An improved method and apparatus for monitoring the concentration of contaminants, including volatile organic compounds, in groundwater is provided comprising a semi-permeable membrane defining an inner chamber. The chamber is carried within a mesh protective sleeve of cover to prevent abrasion or puncture of the chamber. The membrane is permeable to contaminants but impermeable to a reference fluid, which is distilled water. The method of sampling comprises placing the semipermeable membrane chamber, which contains the reference fluid, in contact with contaminated groundwater, thereby allowing contaminants to diffuse through the semipermeable membrane.

10 Claims, 2 Drawing Sheets

PASSIVE WATER SAMPLER AND METHOD OF SAMPLING

BACKGROUND OF THE INVENTION

This invention relates generally to a liquid sampling device, and more particularly to an improved method and apparatus for monitoring the concentration of contaminants, including volatile organic compounds, in groundwater. Various devices exist for sampling a liquid. A known type of passive, multi-layer sampling device which is used to extract groundwater samples is comprised of a rod (or connector rods) with apertures at specific intervals to accommodate dialysis cells.

U.S. Pat. No. 5,454,275 to Kabis discloses a groundwater sampler which makes use of pressure differentials that result during sampling. U.S. Pat. No. 5,147,561 to Burge et al. teaches a sampling device containing a stripping chamber for stripping a groundwater sample of its volatile components at or near the point of collection. U.S. Pat. No. 4,078,433 to McCabe, Jr. et al. discloses a liquid sampling device comprising a length of pipe having a cap screwed onto each end thereof. The upper cap has an aperture for admitting the liquid to be sampled into the pipe. Despite the prior art devices, there is a need for improvement in the art of groundwater sampling. The use of thin semipermeable membrane materials in water sampling devices presents certain problems due to the very sensitive nature of the membrane. Such membrane are easily damaged in the course of use during placement in a well and removal.

SUMMARY OF THE INVENTION

The water sampling apparatus of this invention comprises a reference liquid chamber constructed of a semipermeable material, a protective mesh cover which conforms to the shape and outer surface of the chamber, and associated attaching means for carrying a weight and lowering line for positioning the device in the body of water to be sampled such as a monitoring well. The term "mesh" as used herein means a material of open texture with evenly spaced holes or openings between the threads, lines, or cords like the fabric of a net. The openings are of sufficient size to permit effective contact between the groundwater and the semipermeable material of which the chamber is formed. "Effective contact" means sufficient water to membrane contact to permit equilibration of contaminants between the groundwater and the reference fluid within a reasonable period of time.

Practice of the invention provides a number of advantages including an improved method and apparatus for sampling groundwater; a method and apparatus for sampling groundwater in a test well that does not require purging or bailing of the well; method and apparatus for sampling groundwater that does not require dialysis cells; a method and apparatus for sampling groundwater that utilizes water as a reference liquid or carrier for volatile organic compounds and other contaminants. Use of the protective mesh cover prevents loss of samples resulting from puncture or tearing of the semipermeable membrane chamber or bag caused by contact with sharp or rough parts of the well screen or casing.

The passive water sampler comprises a sample chamber or container constructed of a semipermeable membrane material, the semipermeable membrane being permeable to contaminants and impermeable to a reference fluid; the semipermeable membrane defining an inner chamber therein; and the inner chamber being at least partially filled with the reference fluid such as distilled water, the partially filled chamber semipermeable membrane material being placed in contact with the groundwater thereby allowing the contaminants to diffuse through the semipermeable membrane and into the inner chamber, the concentrations of the contaminants in the groundwater and in the reference fluid coming into equilibrium. In an embodiment the fluid chamber is substantially completely filled with reference fluid. The sample chamber is carried within a protective covering constructed of a mesh material such that the semipermeable membrane is exposed to contact by the well water and is shielded from contact with the inner walls of the bore of the well or any screen lining the bore of the well. The mesh acts to prevent abrasion or puncture of the membrane chamber by any roughness or protrusions inside the well. The mesh cover is constructed of a stretchable plastic which can be expanded to receive the fluid filled bag and then return to its original dimensions and conform to the shape of the bag or chamber. In embodiments the chamber is of tubular shape heat sealed at both ends after at least partially filing with water and the cover is in the form of a sleeve of mesh material into which the tubular chamber can be inserted. It is generally that the fluid chamber be substantially filled with reference fluid.

DETAILED DESCRIPTION

Figure 1:
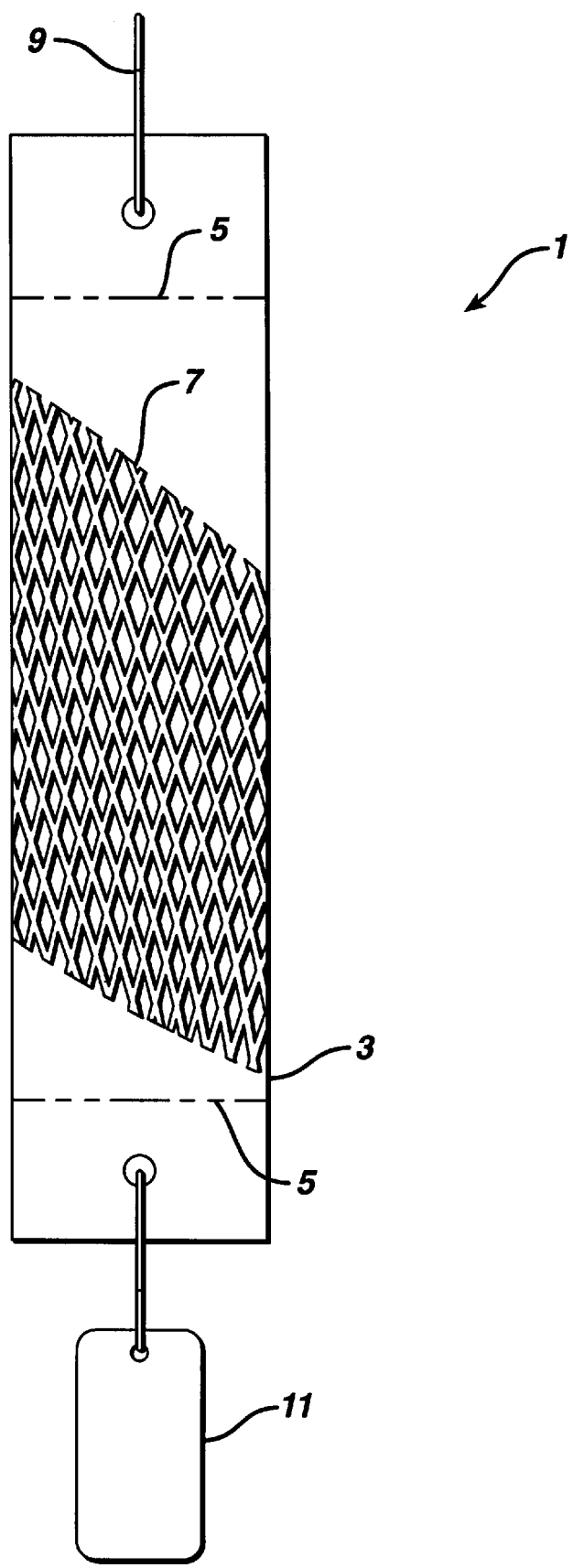
FIG. 1 is a front elevational view of the present invention.
Figure 2:
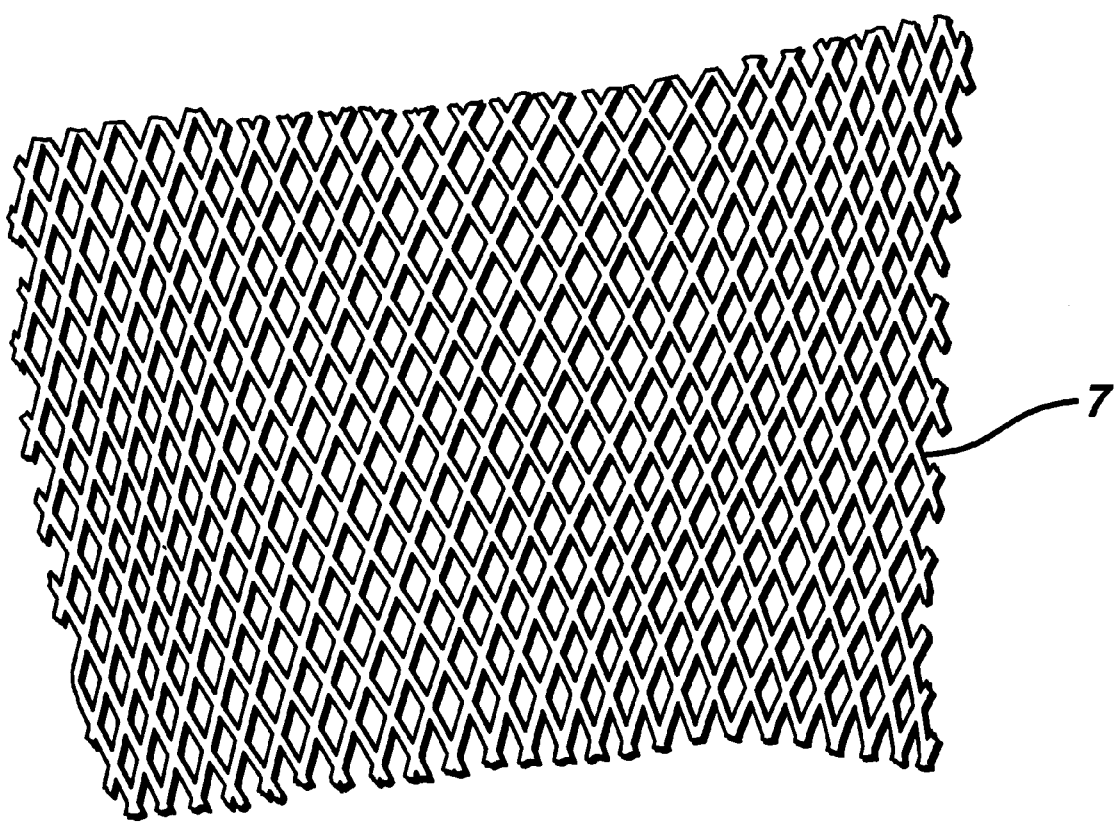
FIG. 2 is plan view of a mesh material suitable for use as the protective cover.

The method and apparatus according to this invention can be used to monitor the concentrations of volatile organic compounds (VOCs) and other contaminants in groundwater in a test or monitoring well without the need to purge or bail the well. Purging a well is presently a regulatory requirement if samples are to be withdrawn from the well, and is a large part of the expense associated with routine monitoring of groundwater contamination. Regulatory agencies typically require removal of at least three casing volumes of water prior to sampling. The large number of observation wells typically sampled at groundwater contamination sites results in a large volume of contaminated purge water that must be disposed of. Thus, sampling costs are incurred which include not only personnel time, but also the proper transport and disposal of the contaminated purge water. These costs can be substantial when multiplied over the lifetime of the contamination. Moreover, the costs associated with remediation and monitoring of existing groundwater contamination must be factored in as a loss when the market value of particular businesses are calculated. The method and apparatus of sampling according to the present invention eliminates the need to purge wells, thus resulting in a substantial cost savings as well as an increased corporate value. Also, the absence of purging makes the present invention environmentally friendly. Use of the protective mesh cover makes the device less subject to accidental damage during use.

Furthermore, the method and apparatus according to the present invention precludes the need for using either dialysis cells or a carbon sorbent. Both of these can be very costly in terms of sampler preparation and analysis. Also, when using a carbon sorbent, the results obtained yield only relative concentrations because the sorbent continues to collect contaminants, including as long as the sampler is in the sampling area. Thus, using the sorbent system, the measured contaminant concentration is a function of the time the sampler was in place. On the other hand, the present invention allows the contaminant concentration in the sampler to change in response to fluctuations in contaminant concentrations outside of the sampler, thereby maintaining equilibrium and providing an accurate contaminant concentration in the sampler at any time after equilibrium is reached. Consequently, great flexibility is allowed in the length of time that the present invention can be left in the sampling area.

Additionally, the present sampling device is used subaqueously, without requiring the pumping or bailing of water samples from within a well. It has been found that water immediately adjacent to a well screen can be representative of an aquifer without having to purge, and may even be more representative than samples obtained after purging due to the sampling bias that can result from the purging itself. The mesh cover prevents damage resulting from contact with the screen or casing of the well.

Referring to the drawings, FIG. 1 shows a front elevational view of a mesh material covered passive water sampler 1 according to the present invention. The water sampler 1 comprises a semipermeable membrane material in the form of a tube 3 with heat seale at the ends 5. Protective mesh 7, shown in partial view, encloses the fluid filled tube Semipermeable membrane 3 is permeable to contaminants but impermeable to the reference fluid, e.g., contaminant-free water. The reference fluid employed is distilled water, but may be undistilled water or any other suitable fluid in which the contaminants are soluble or miscible. Use of distilled water as the reference fluid simplifies the analysis of the sample. Semipermeable membrane 3 can be made from a variety of materials which fit the above-stated criteria but can be made from polyethylene. Polypropylene, may also be employed. Semipermeable membrane 3 may be manufactured in a wide variety of shapes and sizes depending on the application. Water sampler 1 is relatively small, making it easily transportable. Semipermeable membrane 3 defines an internal fluid chamber which can be any size or shape required for use. For example, semipermeable membrane 3 is provided in the shape of a tube having open ends which can be sealed. The inner chamber is formed by sealing the open ends of the tube, thus providing a leakage-free inner chamber. This sealing may be achieved by: heat sealing, sonic welding, or any other suitable bonding method.

Alternatively, the semipermeable membrane may be provided as a flat piece. The chamber is formed by folding the semipermeable material over and onto itself, thereby forming one folded edge and three overlapping edges. The three overlapping edges are respectively sealed.

Prior to placing the water sampler in contact with contaminated groundwater, inner chamber is at least partially filled with the reference fluid in which the contaminants are soluble or miscible and sealed. Other appropriate means for adding or withdrawing fluid may also be employed.

Upon placing a partially filled sampling device 1 in contact with contaminated groundwater, the contaminants begin to diffuse through the semipermeable membrane and into the chamber. The reference fluid does not diffuse into the groundwater. Only contaminants in the groundwater diffuse into the chamber of the device. Contaminants continue to diffuse into the chamber until the concentration of contaminants in the reference fluid and the concentration of contaminants in the groundwater reach equilibrium. As discussed above, water sampler 1 may be submerged in a well for great lengths of time without jeopardizing analysis results. This is because, once equilibrium has been reached, any changes in contaminant concentration outside of water sampler 1 are compensated for by diffusion of contaminants into or out of the chamber. Thus, equilibrium is consistently maintained. For example, if the concentration of contaminants in the groundwater falls, contaminants, will diffuse out of inner chamber 4 and into the groundwater until the contaminant concentrations in the reference fluid and in the groundwater are the same again. Conversely, if the contaminant concentration in the groundwater rises, contaminants, will diffuse from the groundwater into the chamber until the concentrations are the same again.

When water sampler 1 is to be used in a well, support line 9 of suitable length and construction for supporting water sampler 1 while inside a well is attached to the mesh cover by any suitable hook or fastening means. The support line is used to raise water sampler up and out of the well after sampling. The mesh cover serves to prevent abrasion or puncture of the fluid filled device during placement in and removal from the well.

Weight 11 can be hung from the lower portion of the mesh either directly or by a length of support line to assist in submerging water sampler 1 once it is inside of a well. Weights and support lines may be made of a variety of materials and sizes depending on the application.

The method of sampling according to the present invention involves using water sampler 1 in any of its many variations as described above.

The vertical profile of the extent of contamination at different levels in an aquifer can be monitored by setting a series of mesh covered sampling devices at various levels in a monitoring well. Each device will come to equilibrium with the contaminant at the corresponding level in the well.

Sampling is complete when equilibrium has been reached. The sampling device 1 is raised up and out of a well. A portion of the equilibrium mixture of reference fluid and contaminants within the chamber is withdrawn for analysis by cutting the bag or chamber open or by opening any sealed port.

Analysis of the sample is carried out by conventional means, for example, through the use of a gas chromatograph. Because the water adjacent to a well screen in an unpurged well is potentially representative of the water in the adjacent aquifer, the concentration of contaminants in the water sampler can be related to the concentration of contaminants in the aquifer at the screened interval.

At each well to be sampled, an initial comparison should be done between the method of sampling according to the present invention and conventional sampling methods. The purpose of this comparison would be to account for potential borehole-specific interferences and to verify that data obtained using the present invention adequately represents data obtained using the standard sampling methodology.

It is thus seen that an improved method and apparatus for sampling groundwater can be utilized. It is also seen that the method and apparatus for water sampling according to this invention does not require purging of a well. It is also seen that the method and apparatus for water sampling according to this invention can be used subaqueously. It is also seen that the method and apparatus according to this invention precludes the need for using costly sorbents or dialysis cells. It is also seen that the method and apparatus according to this invention can utilize water as a carrier for volatile organic compounds and other contaminants. Furthermore, it is seen that the method and apparatus according to the present invention is economical, environmentally friendly, and easy to construct and use.

Use of a protective mesh cover is a useful and expedient way to reduce loss of water samples resulting from damage to the fluid filled chamber during handling and transportation to and from the well site.

Thin membranes are particularly vulnerable to damage when being placed in a well and when being removed from a well. The mesh cover makes the use of thindifusion films a practical method for monitoring the concentration of contaminants in groundwater.

It is understood that many variations will become apparent to one of ordinary skill in the art upon reading the specification. Such variations are within the spirit and scope of the invention as defined by the following appended claims.

What is claimed:

1. A passive water sampler for monitoring the concentration of contaminants in groundwater comprising:

a semipermeable membrane, said semipermeable membrane being permeable to said contaminants and impermeable to a reference fluid;

said semipermeable membrane defining an inner chamber therein;

said inner chamber being at least partially filled with reference fluid, said partially filled semipermeable membrane placed in contact with said groundwater thereby allowing said contaminants to diffuse through said semipermeable membrane and into said inner chamber, the concentrations of said contaminants in said groundwater and in said reference fluid coming into equilibrium; and an elastic stretchable mesh protective cover surrounding the chamber.

2. The water sampler according to claim 1 wherein said reference fluid is water.

3. The water sampler according to claim 2 wherein said water is distilled water.

4. The water sampler according to claim 1 wherein said semipermeable membrane is made from polyethylene.

5. The water sampler according to claim 1 wherein said semipermeable membrane is provided in generally the shape of a tube having open ends, said open ends being sealed to form said inner chamber.

6. The water sampler according to claim 1 wherein said semipermeable membrane is provided as generally a flat piece, said flat semipermeable membrane being folded over and onto itself thereby creating a folded edge and three overlapping edges, said three overlapping edges being respectively sealed together to form said inner chamber.

7. The water sampler according to claim 1 further comprising a weight and a support line said weight to assist in said water sampler in a well, said line for supporting said water sampler in said well and for raising said water sampler up and out of said well.

8. A method for determining the concentration of contaminants in groundwater comprising the steps of:

providing a semipermeable membrane, said semipermeable membrane being permeable to said contaminants and impermeable to a reference fluid, manipulating said semipermeable membrane to define an inner chamber therein;

at least partially filling said inner chamber with said reference fluid; placing the chamber in an elastic stretchable protective sheath;

placing said partially filled chamber in contact with said groundwater, allowing said contaminants to diffuse through said semipermeable membrane and into said inner chamber;

allowing sufficient time for the concentrations of said contaminants in said groundwater and in said reference fluid to come into equilibrium;

removing said semipermeable membrane from contact with said groundwater;

withdrawing at least a portion of said reference fluid containing said contaminants from said inner chamber for analysis.

9. The method according to claim 8 wherein said step of at least partially filling said inner chamber with said reference fluid further comprises substantially completely filling said inner chamber with distilled water.

10. The method according to claim 8 wherein said step of providing a semipermeable membrane further comprises providing a semipermeable membrane in the shape of a tube having open ends, and wherein said step of manipulating said semipermeable membrane to define an inner chamber therein further comprises sealing said open ends and providing said mesh in the form of a sleeve.

* * * * *